United States Patent [19]

Jakus et al.

[11] Patent Number: 5,344,846
[45] Date of Patent: Sep. 6, 1994

[54] COMPOSITIONS AND METHODS FOR INHIBITING DEOXYHYPUSINE SYNTHASE AND THE GROWTH OF CELLS

[75] Inventors: Judit Jakus, Silver Spring; Myung H. Park, Potomac; Edith C. Wolff, Bethesda; John E. Folk, Derwood, all of Md.

[73] Assignee: The United States of America as represented by the Department of Health and Human Services, Washington, D.C.

[21] Appl. No.: 998,231

[22] Filed: Dec. 30, 1992

[51] Int. Cl.$^5$ ............... C07C 279/04; A61K 31/155
[52] U.S. Cl. ............................. 514/634; 424/2; 424/572; 424/573; 424/574; 514/863; 564/240
[58] Field of Search ............... 564/240; 514/634, 863; 424/2, 572, 573, 574

[56] References Cited

U.S. PATENT DOCUMENTS

| | | | |
|---|---|---|---|
| 3,201,459 | 8/1965 | Coda et al. | 564/240 |
| 5,059,624 | 10/1991 | Monache et al. | 564/240 |

OTHER PUBLICATIONS

M. H. Park et al., *The J. of Biolo. Chem.*, vol. 266, No. 13, pp. 7988–7994, Issue of May 5, 1991.
M. H. Park et al., *The J. of Biolo. Chem.*, vol. 263, No. 30, pp. 15264–15269, Issue of Oct. 25, 1988.
E. C. Wolff et al., *The J. of Biolo. Chem.*, vol. 265, No. 9, pp. 4793–4799, Issue of Mar. 25, 1990.
R. J. Murphey et al., *J. Biolo. Chem.*, vol. 262, pp. 15033–15036 (1987).
E. Höltta et al., *Biochimica et Biophysica Acta*, vol. 677, (1981) pp. 90–102.
L. Alhonen–Hongisto et al., *Biochem. J.*, (1980) vol. 188, pp. 491–501.
C. W. Porter et al., *Cancer Research*, vol. 42, pp. 4072–4078, Oct. 1982.
A. Abbruzzese et al., *Biochimica et Biophysica Acta*, (1989) vol. 997, pp. 248–255.
M. A. Paz et al., (abstract 1352) 76th. *Annual Meeting of the American Society of Biolo. Chem.*, Wash., D.C., USA, p. 1712 (1986).
J. Trijssenaar et al., (abstract 053), *Invest. New Drugs* 7141, p. 362 (1989).
E. C. Wolff et al, (abstract 219) *Faseb J.*, vol. 6, p. A39 (1992).
J. Trijssenaar et al., (abstract 2473), *Proc. of the American Assoc for Cancer Research*, vol. 31, Mar. 1990.
T. L. Byers, et al., *Biochem. J.*, vol. 287, pp. 717–724, (1992) (Printed in Great Britain).

*Primary Examiner*—Peter O'Sullivan
*Attorney, Agent, or Firm*—Townsend and Townsend Khourie and Crew

[57] ABSTRACT

Compositions and methods for the treatment of mammalian cells to inhibit cell growth, especially for inhibiting the proliferative cell growth associated with malignant and non-malignant disease, are provided. More particularly, a deoxyhypusine synthase inhibitor, typically, a mono- or bisguanyl diamine or polyamine, is administered to the cells.

Also provided by this invention are diagnostic methods and kits for screening the cells of a patient to determine the effect of the deoxyhypusine synthase inhibitor on proliferation of the cells.

5 Claims, 6 Drawing Sheets

| NO. | COMPOUND | STRUCTURE | IC$_{50}$ µM | K$_I$ µM |
|---|---|---|---|---|
| 1. | 1,2-DIAMINOETHANE | H$_2$N~NH$_2$ | -a | |
| 2. | 1,3-DIAMINOPROPANE | H$_2$N~~NH$_2$ | 6.3 | 4.0±0.2 |
| 3. | PUTRESCINE | H$_2$N~~~NH$_2$ | 91 | |
| 4. | CADAVERINE | H$_2$N~~~~NH$_2$ | -a | |
| 5. | 1,6-DIAMINOHEXANE | H$_2$N~~~~~NH$_2$ | 171 | |
| 6. | 1,7-DIAMINOHEPTANE | H$_2$N~~~~~~NH$_2$ | 8.1 | 5.6±0.6 |
| 7. | 1,8-DIAMINOOCTANE | H$_2$N~~~~~~~NH$_2$ | 9.1 | 6.2±1.3 |
| 8. | 1,9-DIAMINONONANE | H$_2$N~~~~~~~~NH$_2$ | 216 | 159±16 |
| 9. | CALDINE | H$_2$N~~NH~~NH$_2$ | 41.2 | 28±4 |
| 10. | SPERMIDINE | H$_2$N~~~NH~~~~NH$_2$ | 7.8[b] | 4.5±0.7[c] |
| 11. | N-(3-AMINOPROPYL)-CADAVERINE | H$_2$N~~~NH~~~~~NH$_2$ | 118 | 83±7 |
| 12. | SPERMINE | H$_2$N~~~NH~~~~NH~~~NH$_2$ | -a | | a) LESS THAN 50% INHIBITION AT 1 mM b) APPARENT "INHIBITION" BY UNLABELED SPERMIDINE, UNCORRECTED FOR EITHER DILUTION OF ($^3$H)SPERMIDINE OR FOR THE INCREASE IN SPERMIDINE CONCENTRATION.

c) K$_m$ FOR SPERMIDINE

FIG. 2.

| NO. | COMPOUND | STRUCTURE |
|---|---|---|
| 13. | 1-AMINOOCTANE | $H_2N\sim\sim\sim CH_3$ |
| 14. | N-BUTYL-1,3-DIAMINOPROPANE | $H_2N\sim\sim NH\sim\sim CH_3$ |
| 15. | N-(3-CYANOPROPYL)-1,3-DIAMINO-PROPANE | $H_2N\sim\sim NH\sim\sim C\equiv N$ |
| 16. | N-(2-CYANOETHYL)-1,4-DIAMINO-BUTANE | $N\equiv C\sim NH\sim\sim\sim NH_2$ |
| 17. | PUTREANINE | $HO-\overset{O}{\underset{\|}{C}}\sim NH\sim\sim\sim NH_2$ |
| 18. | $N^1$-ETHYL SPERMIDINE | $CH_3-CH_2-NH\sim\sim NH\sim\sim\sim NH_2$ |
| 19. | $N^3$-ETHYL SPERMIDINE | $H_2N\sim\sim\sim NH\sim\sim NH-CH_2-CH_3$ |
| 20. | $N^1$-ACETYL SPERMIDINE | $CH_3-CO-NH\sim\sim NH\sim\sim\sim NH_2$ |
| 21. | $N^1,N^3$-*BIS TERT*-BUTYLOXY CARBONYL SPERMIDINE | $(CH_3)_3-O-\overset{O}{\underset{\|}{C}}-NH\sim\sim NH\sim\sim\sim NH-\overset{O}{\underset{\|}{C}}-O-(CH_3)_3$ |
| 22. | $N^1,N^7$-*BIS*DIMETHYLCALDINE | $(CH_3)_2N\sim\sim\sim NH\sim\sim\sim N(CH_3)_2$ |
| 23. | $N^1,N^7$-*BIS*ALLYLCALDINE | $\sim NH\sim\sim\sim NH\sim\sim\sim NH\sim$ |
| 24. | $N^1,N^7$-*BIS*BENZYLCALDINE | ⬡$\sim NH\sim\sim\sim NH\sim\sim\sim NH\sim$⬡ |
| 25. | N,N'-*BIS*BENZYLDIAMINO-OCTANE | ⬡$\sim NH\sim\sim\sim\sim\sim NH\sim$⬡ | a) ALL COMPOUNDS LISTED PROVIDED LESS THAN 50% INHIBITION AT 1 mM

*FIG. 3.*

| NO. | COMPOUND | STRUCTURE | IC$_{50}$ μM |
|---|---|---|---|
| 26. | N$^4$-ACETYL SPERMIDINE | 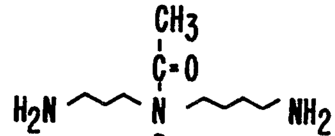 | -a |
| 27. | N$^4$-BROMOACETYL SPERMIDINE | 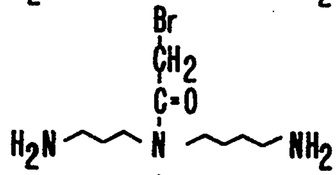 | -a |
| 28. | N$^4$-BENZYL SPERMIDINE | 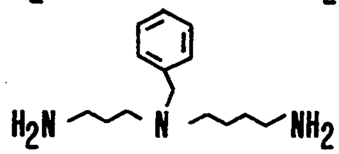 | -a |
| 29. | N$^4$-BENZOYL SPERMIDINE | 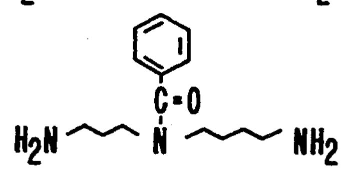 | -a |
| 30. | N$^4$-METHYLCALDINE | 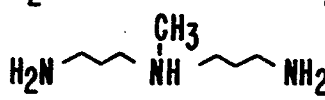 | -a |
| 31. | 1-(3-AMINOPROPYL)-4-AMINOMETHYLPIPERIDINE | 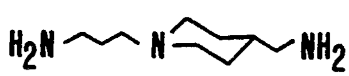 | -a |
| 32. | N-(3-AMINOPROPYL)-CIS-1,4-DIAMINOCYCLOHEXANE $^b$ | 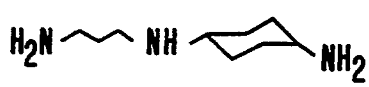 | -a |
| 33. | N-(3-AMINOPROPYL)-TRANS-1,4-DIAMINOCYCLOHEXANE | 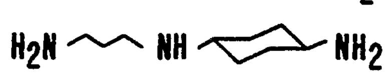 | -a |
| 34. | 5,5-DIMETHYL SPERMIDINE | 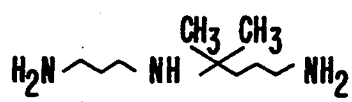 | -a |
| 35. | 1-METHYL SPERMIDINE | 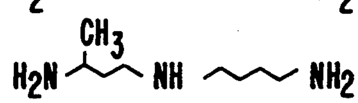 | 184 |
| 36. | 6-FLUOROSPERMIDINE | 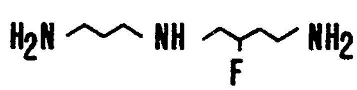 | 48 |
| 37. | 6,6-DIFLUOROSPERMIDINE | 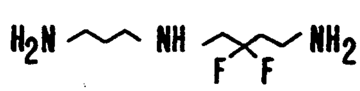 | 14 |
| 38. | 7,7-DIFLUOROSPERMIDINE | 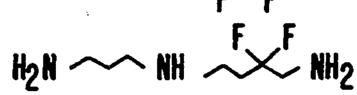 | -a |
| 39. | N-(3-AMINOOXYPROPYL)-1,3-DIAMINOPROPANE | | -a | a) LESS THAN 50% INHIBITION AT 1 mM
b) APPROXIMATELY 80% IN THE CIS FORM, 20% TRANS

FIG. 4.

| NO. | COMPOUND | STRUCTURE | IC$_{50}$ μM | K$_I$ μM |
|---|---|---|---|---|
| 40. | GUAZATINE | H$_2$N-C(=NH)-NH~~~NH~~~NH-C(=NH)-NH$_2$ | 17.2 | 12.1 ±1.6 |
| 41. | N$^1$,N$^6$-*BIS*GUANYL-1,6-DIAMINOHEXANE | H$_2$N-C(=NH)-NH~~~NH-C(=NH)-NH$_2$ | 48.3 | 35.2 ±4.8 |
| 42. | N$^1$,N$^7$-*BIS*GUANYL-1,7-DIAMINOHEPTANE | H$_2$N-C(=NH)-NH~~~NH-C(=NH)-NH$_2$ | 3.0 | 1.7 ±0.08 |
| 43. | N$^1$,N$^8$-*BIS*GUANYL-1,8-DIAMINOOCTANE | H$_2$N-C(=NH)-NH~~~NH-C(=NH)-NH$_2$ | 8.5 | |
| 44. | N$^1$,N$^3$-*BIS*GUANYL-1,3-DIAMINOPROPANE | H$_2$N-C(=NH)-NH~NH-C(=NH)-NH$_2$ | -a | |
| 45. | N$^1$,N$^7$-*BIS*GUANYLCALDINE | H$_2$N-C(=NH)-NH~~NH~~NH-C(=NH)-NH$_2$ | 204 | 154 ±20 |
| 46. | N$^1$-GUANYL-1,3-DIAMINOPROPANE | H$_2$N-C(=NH)-NH~NH$_2$ | -a | |
| 47. | AGMATINE | H$_2$N-C(=NH)-NH~~~NH$_2$ | 71 | |
| 48. | N$^1$-GUANYLCALDINE | H$_2$N-C(=NH)-NH~~NH~~NH$_2$ | 1.2 | 0.74 ±0.03 |
| 49. | N$^1$-GUANYL-1,7-DIAMINOHEPTANE | H$_2$N-C(=NH)-NH~~~NH$_2$ | 0.017 | 0.0097 ±0.0005 |
| 50. | N$^1$-GUANYL-1,8-DIAMINOOCTANE | H$_2$N-C(=NH)-NH~~~NH$_2$ | 0.37 | 0.24 ±0.02 |
| 51. | N$^1$-GUANYLSPERMIDINE | H$_2$N-C(=NH)-NH~~NH~~~NH$_2$ | 0.57 | 0.33 ±0.05 |
| 52. | N$^8$-GUANYLSPERMIDINE | H$_2$N~~NH~~~NH-C(=NH)-NH$_2$ | 0.24 | 0.15 ±0.04 |
| 53. | HIRUDONINE | H$_2$N-C(=NH)-NH~~NH~~~NH-C(=NH)-NH$_2$ | 2.5 | | a) LESS THAN 50% INHIBITION AT 1 mM

*FIG. 5.*

COMPOSITIONS AND METHODS FOR INHIBITING DEOXYHYPUSINE SYNTHASE AND THE GROWTH OF CELLS

BACKGROUND OF THE INVENTION

1. Field of the Invention

This invention relates to compositions and methods for the inhibition of deoxyhypusine synthase, and for the growth inhibition of mammalian cells. More particularly, this invention relates to the administration of mono- and bis-guanyl diamines and polyamines.

2. Description of the Background Art

Malignant diseases are characterized by tumorigenic or neoplastic cell growth. These diseases include malignant hematological systemic diseases, carcinomas, sarcomas, myelomas, melanomas, lymphomas, papillomas, and the like. For example, malignant diseases that can be treated with deoxyhypusine synthase inhibitors include hyperplastic diseases, such as psoriasis, polyposis, hemangiomas, warts, Cushing's disease, goiter, and the like. (See, e.g., V. T. DeVita, Jr., et al., *Cancer: Principles & Practice of Oncology*, 2nd Ed., J. B. Lippincott Co. (1985)). Non-malignant neoplastic diseases are characterized by an undesirable proliferation of cells which is localized to the site of origin, such as benign growths. The transformation of normal cells within the body into either malignant or non-malignant neoplasms may be induced by chemical carcinogens, radiation, physical agents, or spontaneous tumorigenic growth.

The precise etiology of many malignant and non-malignant diseases remains unknown. Accordingly, treatments for these diseases are limited, and effective agents are not always consistently available for a specific disease. These diseases have been treated, for example, by surgical techniques or by non-surgical methods, including chemotherapy, radiation, and immunotherapy. Any value of such treatment techniques, however, is often diminished by adverse side effects or risks attendant with their use. For example, non-surgical techniques such as chemotherapy generally have immunosuppressant effects and may increase the patient's susceptibility to secondary infections. Surgical treatments to excise malignant or nonmalignant tumors involve risks which accompany any invasive procedure and may not effectively remove or eliminate the entire transformed cell population. Moreover, certain malignant diseases are resistant to conventional treatment techniques. For example, most skin melanomas are considered to be radio-resistant.

To date, therefore, conventional methods and therapeutic agents have not proved to be effective or reliable for the treatment of malignant diseases and cell proliferation. For these reasons it would be desirable to provide improved methods which avoid the disadvantages of conventional agents and methods while providing effective and reliable results. Cells that are prevented from forming new proteins as a result of the inhibition of hypusine synthesis in the eukaryotic translation initiation factor 5A are not able to proliferate. Therefore, the inhibition of this amino acid's formation can provide novel methods for the prevention of cell proliferation.

SUMMARY OF THE INVENTION

This invention provides compositions and methods for the in vitro and in vivo treatment of mammalian cells to inhibit cell growth, particularly for inhibiting the proliferative cell growth associated with malignant and non-malignant diseases. More particularly, a deoxyhypusine synthase inhibitor is administered to the mammalian cells. In a particular embodiment, the deoxyhypusine synthase inhibitor will be administered to a mammalian host suffering from a disease associated with abnormal cellular proliferation.

In some embodiments, the deoxyhypusine synthase inhibitor is a compound having the formula:

$$A-(CR^1R^2)_n-NH-(C=NH)-NH_2$$

where A is selected from the group consisting of $-NH_2$ and $-NH-(C=NH)-NH_2$; $R^1$ and $R^2$ are independently selected from the group consisting of hydrogen, halogen, lower alkyl, hydroxyl, lower alkoxy, lower alkoxycarbonyl, lower alkylcarbonyl, and carboxyl; and n is an integer from four to nine. More preferred are those compounds where $R^1$ and $R^2$ are both hydrogen and n is seven or eight. Particularly preferred deoxyhypusine synthase inhibitors include: $N^1$-guanyl-1,7-diaminoheptane, $N^1$,$N^7$-bisguanyl-1,7-diaminoheptane, $N^1$-guanyl-1,8-diaminooctane, and $N^1$,$N^8$-bisguanyl-1,8-diaminooctane.

In other embodiments, the deoxyhypusine synthase inhibitor will be a compound having the formula:

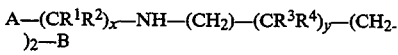

$$A-(CR^1R^2)_x-NH-(CH_2)-(CR^3R^4)_y-(CH_2)_2-B$$

where A and B are independently selected from the group of $-NH_2$ and $-NH-(C=NH)-NH_2$; $R^1$, $R^2$, $R^3$, and $R^4$ are independently selected from the group consisting of hydrogen, halogen, lower alkyl, hydroxyl, lower alkoxy, lower alkoxycarbonyl, lower alkylcarbonyl, and carboxyl; x is an integer form one to three and y is an integer from zero to two, provided that when A and B are both $-NH_2$; and $R^1$, $R^2$, $R^2$, and $R^4$ are all hydrogen; x is not three. More preferred are those compounds where A is $-NH-(C=NH)-NH_2$, B is $-NH-(CH=NH)-NH_2$ or $-NH_2$, $R^1$, $R^2$, $R^3$, and $R^4$ are hydrogen, x is three, and y is one. Particularly preferred deoxyhypusine inhibitors within this class include: $N^1$-guanylcaldine, $N^1$,$N^7$-bisguanylcaldine, $N^1$-guanylspermidine, $N^8$-guanylspermidine, and hirudonine.

Further provided by this invention are compounds having the formula:

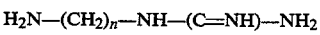

$$H_2N-(CH_2)_n-NH-(C=NH)-NH_2$$

where n is seven or eight.

Also provided by this invention are diagnostic methods and kits for screening cells for susceptibility to treatment with a deoxyhypusine synthase inhibitor, whereby cells are isolated or removed from a patient and treated with a deoxyhypusine synthase inhibitor, then the inhibitor's effect on cellular proliferation is determined. The diagnostic kit typically will comprise a deoxyhypusine synthase inhibitor(s) and other reagents, including a means for detecting the therapeutic effectiveness of the inhibitor on the cells.

BRIEF DESCRIPTION OF THE DRAWINGS

FIG. 2 is a tabular listing of inhibition rates of deoxyhypusine synthase by a variety of diamines and polyamines.

FIG. 3 is a tabular listing of some of the amines with a single primary amino group or with derivatized amino groups which were tested as potential inhibitors of deoxyhypusine synthase.

FIG. 4 is a tabular listing of inhibition rates of deoxyhypusine synthase by a variety of polyamines with substitutions on the secondary amino group or in the carbon chain.

FIG. 5 is a tabular listing of inhibition rates of deoxyhypusine synthase by a variety of guanylated diamines and polyamines.

DETAILED DESCRIPTION OF THE INVENTION

1. Definitions and General Parameters

Figure 1:
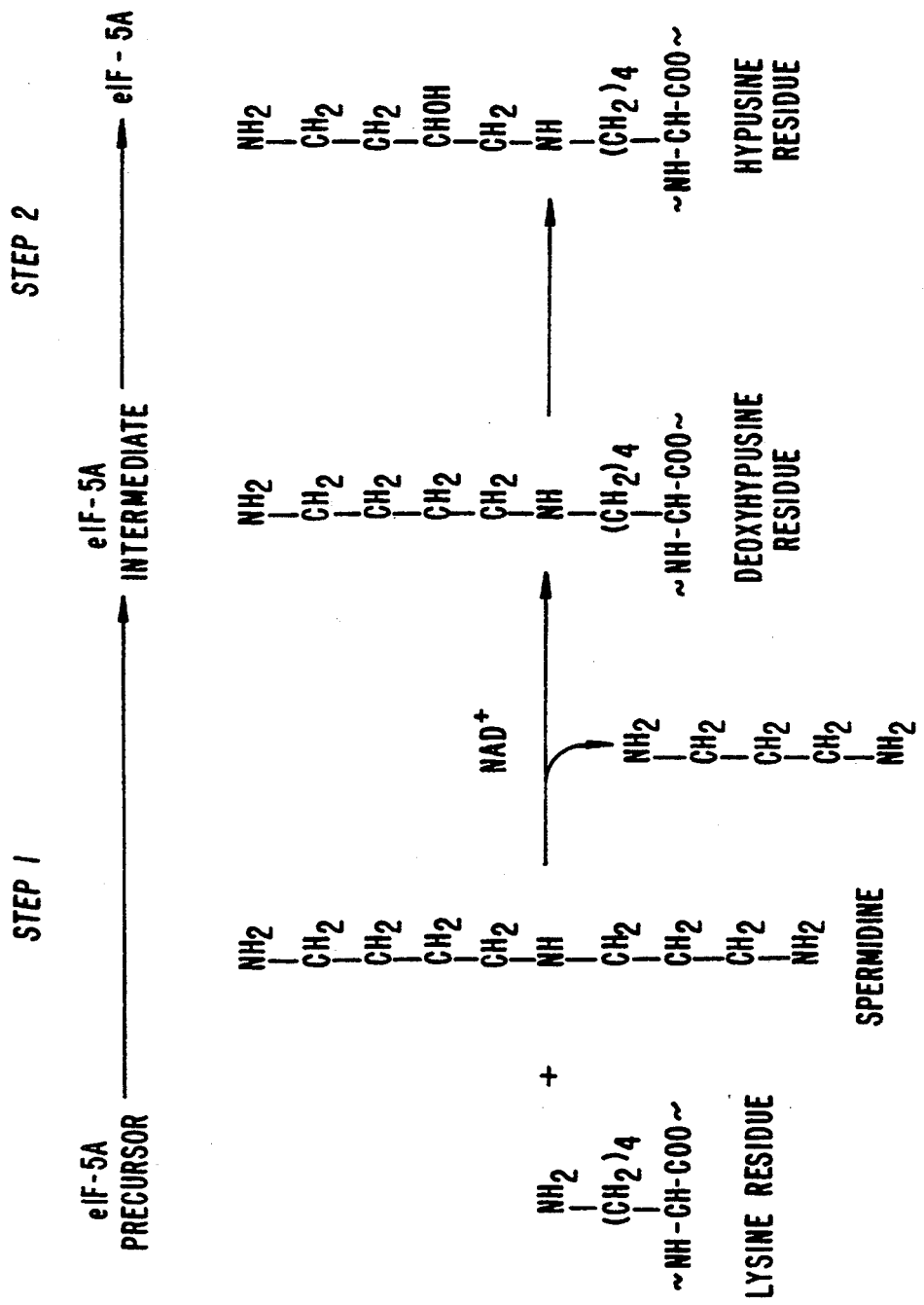
FIG. 1 is a schematic representation of the synthesis of hypusine from spermidine.

Unless otherwise stated, the following terms used in the specification and claims have the meanings given below:

"eIF-5A" refers to eukaryotic translational initiation factor 5A. The nomenclature for initiation factors has been revised (IUB-NC (1989) *Eur. J. Biochem.* 186:1–3). In earlier studies eIF-5A was termed eIF-4D (or IF-M2Bα).

"Treatment" refers to any administration of a deoxyhypusine synthase inhibitor for inhibiting mammalian cell growth in vitro or in vivo and/or mediating the effects of malignant and non-malignant neoplastic diseases, and includes:

(i) inhibiting the symptoms of the disease;
(ii) lessening or inhibiting the long term effects of the disease;
(iii) relieving the symptoms of the disease.

"Pharmacologically effective amount" as applied to the deoxyhypusine inhibitor refers to the amount of component sufficient to induce a desired biological result. That result may be alleviation of the signs, symptoms, or causes of a disease, or any other desired alteration of a biological system. In the present invention, the result will involve the inhibition of cellular growth in a mammalian host, usually the growth inhibition of abnormally proliferative cells.

"Pharmaceutically acceptable" refers to a carrier medium which does not interfere with the effectiveness of the biological activity of the active ingredients and which is not toxic to the hosts to which it is administered.

"Alkyl", denoted generally by R, e.g., by $R^1$, $R^2$, $R^3$, or $R^4$ refers to straight or branched chain aliphatic groups having 1–12 carbon atoms. Those alkyl groups having 1–8 carbon atoms, and especially those having 1–3 carbon atoms, are presently preferred. Alkyl groups include those exemplified by methyl, ethyl, sec-butyl, heptyl, and dodecyl. If more than one alkyl group is present in a given molecule, each may be independently selected from "alkyl" unless otherwise stated.

"Lower alkyl" refers to an alkyl group of one to six carbon atoms. Lower alkyl groups include those exemplified by methyl, ethyl, n-propyl, i-propyl, n-butyl, t-butyl, i-butyl (2-methylpropyl), i-amyl, n-amyl and hexyl. Preferred lower alkyls are methyl and ethyl. If more than one alkyl group is present in a given molecule, each may be independently selected from "lower alkyl" unless otherwise stated.

"Halogen" refers to chlorine, bromine, fluorine and iodine.

"Lower alkoxy" refers to a lower alkyl group attached through an oxygen atom.

"Hydroxyl" refers to the group —OH.

"Carboxyl" refers to the group —COOH.

"Carbonyl" refers to the group —C=O.

2. The Deoxyhypusine Pathway

Deoxyhypusine ($N^\epsilon$-(4-aminobutyl)lysine) is an intermediate in the post-translational biosynthesis of the unique amino acid hypusine ($N^\epsilon$-(4-amino-2-hydroxybutyl)lysine). Hypusine occurs at a single position in one cellular protein, the eukaryotic translation initiation factor 5A (eIF-5A). eIF-5A, abundant in all eukaryotic cells examined, appears to be essential for protein synthesis and for cell growth. (See, e.g., Cooper et al. (1982) *Cell* 29:791–797; and Schnier et al. (1991) *Mol. Cell. Biol.* 11:3105–3114.)

The formation of hypusine occurs in two steps through modification of a lysine residue in the protein precursor of eIF-5A. As shown in FIG. 1, the enzyme deoxyhypusine synthase catalyzes the first step, in which the 4-aminobutyl moiety of the polyamine spermidine is transferred to the ε-amino group of a specific lysine residue of the precursor to form the deoxyhypusine residue. (See Park et al. (1982) *J. Biol. Chem.* 257:7217–7222; Park et al. (1988) *J. Biol. Chem.* 263:15264–15269; and Wolff et al. (1990) *J. Biol. Chem.* 265:4793–4799.) In the absence of the eIF-5A precursor deoxyhypusine synthase catalyzes the cleavage of spermidine to form $\Delta^1$-pyrroline and 1,3-diaminopropane. The occurrence of this partial reaction suggests that association of spermidine with the enzyme is an early event during catalysis and is independent of binding of the eIF-5A protein precursor.

Deoxyhypusine synthase, purified approximately 700-fold from rat testis, exhibits an apparent molecular mass of 180–190 kDa upon size exclusion chromatography. (See Wolff et al. (1990) *J. Biol. Chem.* 265:4793–4799.) The K$_{m(app)}$ values for the substrates, spermidine, NAD$^+$ and eIF-5A precursor from spermidine-depleted CHO cells, have been calculated as approximately 4, 30, and 0.08 µM, respectively.

The enzyme displays a quite narrow specificity for all of its substrates. Although NADP+ and NADH were reported to substitute for NAD+ to some degree with crude enzyme preparations, their effects with the more purified enzyme were found to be negligible. Neither free lysine nor synthetic 9- or 16-member peptides modeled on the amino acid sequence encompassing the lysine residue in eIF-5A precursors that undergoes modification to hypusine, function as substrates for deoxyhypusine synthase. An eIF-5A precursor, ec-eIF-5A(Lys) [the eIF-5A precursor containing unmodified Lys prepared by over-expression of human eIF-5A cDNA in *E. coli*], is a good substrate. (See Smit-McBride et al. (1989) *J. Biol. Chem.* 264:18527–18530; Wolff et al. (1990) *J. Biol. Chem.* 265:4793–4799; and Park et al. (1991) *J. Biol. Chem.* 266:7988–7994.) In contrast, an altered eIF-5A precursor protein, in which $Lys^{50}$ is replaced by Arg, is not, indicating that only lysine is modified by deoxyhypusine synthase. This finding is consistent with the conclusion that this lysine is the only one in the precursor that is converted to hypusine, both in cells and in the enzyme reaction in vitro.

From the results contained herein, it can be postulated that the spermidine binding site of deoxyhypusine synthase is located not totally on the surface of the molecule, but rather, at least partially, within a restricted region. It is possible to contrive several models for this type of binding site that are consistent with the data. One of these envisions the restricted region as a pocket into which the aminopropyl portion, the secondary amino group, and the carbon 5 of spermidine must be inserted. This pocket contains at its apex or nadir the amine binding site and, less than 4.9 Å from this site, the point at which the secondary amino group must be oriented for cleavage. The other amine binding site is on the surface of the enzyme. The dimensions of the pocket are such that it will not accommodate the branch formed by a methyl group or larger group on any carbon atom or on the secondary nitrogen of a polyamine.

There is substantial evidence that hypusine, and possibly deoxyhypusine, plays a vital role in the biological activity of eIF-5A. (See, e.g., Park (1989) *J. Biol. Chem.* 264:18531–18535; Smit-McBride et al. (1989) *J. Biol. Chem.* 264:18527–18530; and Park et al. (1991) *J. Biol. Chem.* 266:7988–7994.) Thus, the inhibition of spermidine association with deoxyhypusine synthase would prevent formation of deoxyhypusine, and hence selectively block the production of biologically active forms of eIF-5A protein. This evidence for disruption of the initial step in the post-translational maturation of eukaryotic initiation factor 5A provides a basis for the potential control of protein biosynthesis and cell proliferation.

3. Deoxyhypusine Synthase Inhibitors

In a preferred embodiment of this invention, aliphatic diamines and polyamines are employed as deoxyhypusine synthase inhibitors. The efficiency of binding of aliphatic diamines and polyamines to deoxyhypusine synthase, and hence, their efficacy as inhibitors, are related to a variety of factors, including: 1) the distance between their primary amino groups; 2) the presence of two charged primary amino groups, or two charge guanidino groups, or one of each; 3) the substitution patterns at the secondary amino groups, if present, and at certain positions in their carbon chains.

Preferred deoxyhypusine inhibitors are of two general types. For both types of inhibitors, the mono-guanyldiamines typically will be more effective as inhibitors than their bis-guanyldiamine counterparts.

Type I inhibitors are of the following formula:

$$A-(CR^1R^2)_n-NH-(C=NH)-NH_2$$

where A is selected from the group consisting of $-NH_2$ and $-NH-(C=NH)-NH_2$; $R^1$ and $R^2$ are independently selected from the group consisting of hydrogen, halogen, lower alkyl, hydroxyl, lower alkoxy, lower alkoxycarbonyl, lower alkylcarbonyl, and carboxyl; and n is an integer from four to nine.

Preferably, Type I inhibitors will have the following structure:

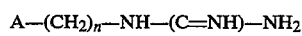
$$A-(CH_2)_n-NH-(C=NH)-NH_2$$

where A is $-NH_2$ or $-NH-(C=NH)-NH_2$; and n is an integer from four to nine. In a most preferred embodiment, n is seven or eight.

Examples of preferred Type I inhibitors include $N^1$-guanyl-1,7-diaminoheptane, $N^1,N^7$-bisguanyl-1,7-diaminoheptane, $N^1$-guanyl-1,8-diaminooctane, and $N^1,N^8$-bisguanyl-1,8-diaminooctane.

Type II deoxyhypusine synthase inhibitors have the following formula:

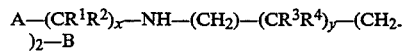
$$A-(CR^1R^2)_x-NH-(CH_2)-(CR^3R^4)_y-(CH_2)_2-B$$

where A and B are independently selected from the group consisting of $-NH_2$ and $-NH-(C=NH)-NH_2$; $R^1$, $R^2$, $R^3$, and $R^4$ are independently selected from the group consisting of hydrogen, halogen, lower alkyl, hydroxyl, lower alkoxy, lower alkoxycarbonyl, lower alkylcarbonyl, and carboxyl; x is an integer from one to three and y is an integer from zero to two, provided that when A and B are $-NH_2$, x is not three if $R^1$, $R^2$, $R^3$, and $R^4$ are hydrogen.

More typically, the Type II inhibitors will have the following formula:

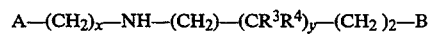
$$A-(CH_2)_x-NH-(CH_2)-(CR^3R^4)_y-(CH_2)_2-B$$

where A and B are independently selected from the group consisting of $-NH_2$ and $-NH-(C=NH)-NH_2$; $R^3$ and $R^4$ are independently selected from the group consisting of hydrogen, halogen, lower alkyl, hydroxyl, lower alkoxy, lower alkoxycarbonyl, lower alkylcarbonyl, and carboxyl; x is an integer from one to three; and y is an integer from zero to two, provided that when A and B are $-NH_2$, x is not three if $R^3$ and $R^4$ are hydrogen.

In a more preferred embodiment, the Type II inhibitor will have the following formula:

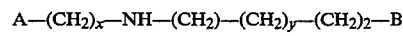
$$A-(CH_2)_x-NH-(CH_2)-(CH_2)_y-(CH_2)_2-B$$

where A and B are independently selected from the group consisting of $-NH_2$ and $-NH-(C=NH)-NH_2$; x is an integer from one to three; and y is an integer from zero to two, provided that when A and B are $-NH_2$, x is not three.

Particularly preferred Type II inhibitors include those shown in the following table:

| A | B | x | y |
| --- | --- | --- | --- |
| $-NH_2$ | $-NH_2$ | 1-3 | 0-2 |

-continued

| A | B | x | y |
| --- | --- | --- | --- |
| —NH$_2$ | —NH—(C=NH)—NH$_2$ | 1-3 | 0-2 |
| —NH—(C=NH)—NH$_2$ | —NH$_2$ | 1-3 | 0-2 |
| —NH—(C=NH)—NH$_2$ | —NH—(C=NH)—NH$_2$ | 1-3 | 0-2 |

Examples of these particularly preferred inhibitors include: N$^1$-guanylcaldine, N$^1$,N$^7$-bisguanylcaldine, N$^1$-guanylspermidine, N$^8$-guanylspermidine, and hirudonine.

Many of the deoxyhypusine synthase inhibitors of the present invention are commercially available. Others can be obtained by known techniques from readily available starting materials, as described in greater detail below. (See, Park et al. (1988) *J. Biol. Chem.* 263:15264–15269; Wolff et al. (1990) *J. Biol. Chem.* 265:4793–4799; and Park et al. (1991) *J. Biol. Chem.* 266:7988–7994).)

4. In Vitro Uses

The compositions and methods of the present invention can be used in vitro for testing hyper- and neoplastic cell susceptibility to varying treatment regimens. Thus, the invention also includes an in vitro diagnostic method whereby cells taken from a patient suffering from proliferative cell growth associated with a malignant or non-malignant disease are treated with a deoxyhypusine synthase inhibitor to determine the effectiveness and amount of the inhibitor necessary to inhibit cellular proliferation. Cells or a biological sample containing cells from a host or an organ of a host are first isolated from the patient. The sample containing the cells, or the isolated cells themselves, is maintained in vitro and is then contacted with one or more inhibitors of the present invention. The inhibitor and dosage can be varied. The activity of the inhibitor can be measured by its ability to reduce cellular proliferation and/or damage or kill cells in culture. This can be readily assessed by vital staining techniques. See, e.g., Naughton et al. (1991) U.S. Pat. No. 5,032,509. After the inhibitors are screened, then the appropriate treatment and dosage can be selected by the physician and administered to the patient based upon the results. Therefore, this invention also contemplates use of inhibitors of this invention in a variety of diagnostic kits and assay methods.

Frequently, the reagents for diagnostic assays are supplied in kits, so as to optimize the sensitivity of the assay. For the subject invention, depending upon the nature of the assay, the protocol, and the label, either labeled or unlabeled material is provided, usually in conjunction with other additives, such as buffers, stabilizers, materials necessary for signal production such as substrates for enzymes, and the like. Desirably, the reagents are provided as a dry powder, where the reagents can be reconstituted in an aqueous medium having appropriate concentrations for performing the assay. The invention provides a diagnostic kit which is useful for detecting the anti-cellular proliferation therapeutic effectiveness of a deoxyhypusine synthase inhibitor on cells. This kit comprises a deoxyhypusine synthase inhibitor and other reagents including a means for detecting the therapeutic effectiveness of the antagonist on the cells.

Any of the aforementioned constituents of the diagnostic assays can be used without modification or can be modified in a variety of ways; for example, by labeling, such as covalently or non-covalently joining a moiety which directly or indirectly provides a detectable signal. In any of these assays, the materials thereto can be labeled either directly or indirectly. Possibilities for direct labeling include label groups such as: radiolabels such as $^3$H and fluorescent labels (U.S. Pat. No. 3,940,475) capable of monitoring the change in fluorescence intensity, wavelength shift, or fluorescence polarization. Possibilities for indirect labeling include biotinylation of one constituent followed by binding to avidin coupled to one of the above label groups.

5. In Vivo Uses

While it is possible to administer the active ingredient of this invention alone, it is preferable to present it as part of a pharmaceutical formulation. The formulations of the present invention comprise at least one compound of this invention in a therapeutically- or pharmaceutically-effective dose together with one or more pharmaceutically or therapeutically acceptable carriers and optionally other therapeutic ingredients. Various considerations are described, e.g., in Gilman et al. (eds) (1990) *Goodman and Gilman's: The Pharmacological Bases of Therapeutics*, 8th Ed., Pergamon Press; and *Remington's Pharmaceutical Sciences*, Mack Publishing Co.: Easton, Pa., 17th Ed. (1985). Methods for administration are discussed therein, e.g., for oral, intravenous, intraperitoneal, or intramuscular administration, and others. Pharmaceutically acceptable carriers will include water, saline, buffers, and other compounds described, e.g., in the Merck Index, Merck & Co., Rahway, N.J.

The pharmaceutical compositions generally will be administered by parenteral administration for prophylactic and/or therapeutic treatment. The pharmaceutical compositions can be administered in a variety of unit dosage forms depending upon the method of administration. For example, unit dosage forms suitable for oral administration include powder, tablets, pills, capsules and dragees.

The pharmaceutical compositions will often be administered intravenously. Thus, this invention provides compositions for intravenous administration which comprise a solution of the compound dissolved or suspended in an acceptable carrier, preferably an aqueous carrier. A variety of aqueous carriers can be used, e.g., water, buffered water, 0.9% saline, and the like. These compositions will sometimes be sterilized by conventional, well known sterilization techniques, or can be sterile filtered. The resulting aqueous solutions can be packaged for use as is, or lyophilized, the lyophilized preparation being combined with a sterile aqueous solution prior to administration. The compositions can contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, and the like.

For solid compositions, conventional nontoxic solid carriers can be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 0.1–95% of active ingredient, preferably about 20%.

In therapeutic applications, compositions are administered to a patient in an amount sufficient to at least partially inhibit cell proliferation. An amount adequate to accomplish this is defined as "therapeutically-effective amount or dose." Amounts effective for this use will depend on the inhibition desired and the weight and general state of the patient.

Compounds will preferably be administered in a daily dose, generally in a range from about 0.01 mg to about 100 mg per kilogram of body weight per day. A more preferred dosage will be a range from about 1 mg to about 50 mg per kilogram of body weight. Most preferred is a dosage in a range of about 2 to about 10 mg per kilogram of body weight per day.

A suitable dose can be administered in multiple sub-doses per day. These sub-doses can be administered in unit dosage forms. Typically, a dose or sub-dose can contain from about 0.01 mg to about 100 mg of active compound per unit dosage form.

It is preferred that the compositions of this invention be administered locally near or within the undesired cell proliferation site; thereby minimizing disruption of normal surrounding tissues.

In order that the invention described herein can be more fully understood, the following examples are set forth. It should be understood that these examples are for illustrative purposes only, and are not to be construed as limiting this invention in any manner.

EXPERIMENTAL PROCEDURES

Materials

[1,8-$^3$H]Spermidine·3HCl(20–30 Curies (Ci)/millimoles (mmol)) was purchased from DuPont-New England Nuclear (Boston, Mass.); 1-aminooctane and $N^4$-methylcaldine from Aldrich Chemical Company (Milwaukee, Wis.); caldine from Eastman Chemicals (Kingsport, Tenn.); hirudonine·1.5H$_2$SO$_4$ from ICN Biochemicals (Cosa Mesta, Calif.); putreanine.HCl from Vega (Tucson, Ariz.); and $N^1$-acetylspermidine.2HCl, $N^4$-benzylspermidine, and agmatine.H$_2$SO$_4$ from Sigma (St. Louis, Mo.). N-Butyl-1,3-diaminopropane.2HCl (MDL 73208), N,N'-bisdimethylcaldine.3HCl (MDI 27483), N,N'-bisallylcaldine.3HCl (MDL 27305), N,N'-bisbenzylcaldine.3HCl (MDL 27616), N,N'-bis-benzyl-1,8-diaminooctane.2HCl (MDL 27617), 6-fluorospermidine.3HBr (MDL 72721), 6,6-difluorospermidine.3HBr (MDL 72766) and 7,7-difluorospermidine.3HBr (MDL 72748) were generous gifts from Drs. N. Seiler, P. S. Mamont, and R. Snyder, Merrell Dow Research Institutes of the Marion Merrell Dow Inc. (Strasbourg, France); 5,5-dimethylspermidine.3HCl from Dr. B. Ganem, Cornell University; and 1-methylspermidine.3HCl from Dr. J. K. Coward, University of Michigan. The following compounds were prepared by the referenced procedures: N-(3-aminopropyl) cadaverine.3HCl (Park et al. (1991) *J. Biol. Chem.* 266:7988–7994); N-(3-cyanopropyl)-1,3-diaminopropane.2HCl (Abbruzzese et al. (1989) *Biochem. Biophys. Acta* 997:248–255); N-(2-cyanoethyl)-1,4-diaminobutane.2HCl (id.), $N^1N^8$-bis tert butyloxycarbonyl (Boc) spermidine (Nagarajan et al. (1985) *J. Org. Chem.* 50:5735–5737); $N^4$-benzoylspermidine.2F$_3$CCOOH (Bergeron et al. (1982) *Synthesis* 689–692); and N-(3-aminooxypropyl)-1,3-diaminopropane.3HCl (Khomutov, A. R., and Khomutov, R. M. (1989) *Bioorg. Khim.* 15:698–703). The eIF-5A precursor protein, ec-eIF-5A(Lys) was prepared in the Laboratory of Dr. J. W. B. Hershey, University of California, Davis, Calif., by overexpression of a human eIF-5A cDNA in *E. coli* as described previously (Smit-McBride et al. (1989) *J. Biol. Chem.* 264:18527–18530) and further purified on a Mono S column. Deoxyhypusine synthase was prepared from rat testis (Wolff et al. (1990) *J. Biol. Chem.* 265:4793–4799). The specific activity of the enzyme preparation used was 13,000 units per milligram (mg).

Other compounds, materials, and reagents are described in earlier publications (see Park and Wolff (1988) *J. Biol. Chem.* 263:15264–15269; Wolff et al. (1990) *J. Biol. Chem.* 265:4793–4799; and Park et al. (1991) *J. Biol. Chem.* 266:7988–7994).

Synthesis of Compounds

All of the following compounds and the intermediates in their preparations were examined by mass spectrometry. The positive ion fast atom bombardment mass spectral data for the guanidines were found to be consistent with their assigned structures as were the chemical ionization mass spectral data for all other compounds. Thin layer chromatography and elemental analyses provided evidence of purity of the compounds. Values obtained upon elemental analysis were in accordance with the expected salt compositions and were the basis for assignment of hydrate contents of appropriately dried compounds.

Guanidines $N^1$-Guanylspermidine-1.5H$_2$SO$_4$.2H$_2$O, melting point (m.p.) 75° C., and $N^8$-guanylspermidine.3HCl.1.5-H$_2$O, m.p. 110° C., were prepared from $N^8$-acetylspermidine (Sigma) and $N^1$-acetylspermidine, respectively, by reaction with 0-methylisourea hydrogen sulfate (Aldrich) in water (see Taylor et al. (1972) British Patent 1,294,443), followed by removal of the acetyl blocking groups by hydrolysis in 2.5 normal (N) hydrochloric acid (HCl). Purifications were carried out by ion exchange chromatography as outlined in Robin et al. (1967) *Comp. Biochem. Physiol.* 22:787–797. $N^8$-Guanylspermidine was crystallized as the hydrochloride salt from water-methanol. $N^1$-Guanylspermidine was crystallized from the same solvent mixture, but only after its conversion to the hydrogen sulfate salt by addition of a slight excess of sulfuric acid.

$N^1$-Guanyl-1,3-diaminopropane.2HCl, m.p. 154° C., and $N^1$-guanylcaldine.3HCl, m.p. 260° C., were obtained from diaminopropane and caldine, respectively, by reaction with one-half equivalent of the above reagent in water. The products were isolated by chromatography as above and crystallized from water-methanol.

$N^1$, $N^3$-bisguanyl-1,3-diaminopropane.H$_2$SO$_4$.H$_2$O, $N^1$,$N^6$-bisguanyl-1,6-diaminohexane.H$_2$SO$_4$, $N^1$,$N^7$-bisguanyl-1,7-diaminoheptane.H$_2$SO$_4$, $N^1$,$N^8$-bisguanyl-1,7-diaminooctane.H$_2$SO$_4$ and $N^1$,$N^7$-bisguanyl caldine.1.5H$_2$SO$_4$ were prepared by reaction of the parent amines and caldine, respectively, with the guanylating reagent in water (see Taylor supra). The products separated readily from the reaction mixtures and were purified by recrystallization from water-methanol. Melting points for compounds isolated as hydrogen sulfate salts are not reported, since most of them decomposed at temperatures above 300° C.

$N^1$-Guanyl-1,7-diaminoheptane.H$_2$SO$_4$ and $N^1$-guanyl-1,8-diaminooctane.H$_2$SO$_4$ were prepared through the following series of reactions. N,N'-bis-Benzyloxycarbonyl (Z)-1,7-diaminoheptane, m.p. 90° C. (61% yield) and N,N'-bis-Z-1,8-diaminooctane, m.p. 123° C.

(86% yield), obtained by the method described for the synthesis of N,N'-bis-Z-cadaverine (see Clarke et al. (1959) *Arch. Biochem. Biophys.* 79:338–354), were dissolved in dichloromethane (50 millimoles (mmol)/50 milliliters (ml)) and treated with 30 weight percent (wt. %) hydrogen bromide in acetic acid (12.5 ml). After 30 minutes the crude mono-Z diamine HBr salts that precipitated were collected by suction filtration. The precipitate obtained from the diaminoheptane derivative was washed on the filter extensively with a 2:1 mixture of dichloromethane-ether; the precipitate obtained from the diaminooctane derivative with dichloromethane. Two recrystallizations from boiling water gave mono-Z-1,7-diaminoheptane. HBr, m.p. 114°–116° C. in 30% yield and mono-Z-1,8-diaminooctane. HBr, m.p. 157° C. in 22% yield. Conversions of these mono-Z derivatives to the N-Z-N'-guanyl intermediates were carried out using one equivalent of gunaylating agent, O-methyl isourea hydrogen sulfate. N-Z-N'-guanyl-1,7-diaminoheptane.$0.5H_2SO_4$, m.p. 124° C., and N-Z-N'-guanyl-1,8-diaminooctane.$0.5H_2SO_4$, m.p. 135° C., were obtained in crystalline form from methanol-water. The intermediates were hydrogenated in methanol containing one equivalent of sulfuric acid ($H_2SO_4$) for 30 minutes at 40 pounds/square inch (lbs/in$^2$) in the presence of palladium on charcoal catalyst. The crystalline N-guanyl diamine salts were obtained from water-methanol in ~65% yield based on the mono-Z-diamine salts.

N-Substituted spermidines $N^1$-Ethylspermidine.3HCl and $N^8$-ethylspermidine.3HCl were prepared from $N^1$-acetylspermidine and $N^8$-acetylspermidine, respectively, by reduction using diborane (see Brown et al. (1973) *J. Org. Chem.* 38: 912–916). The reactions were conducted on the free bases prepared from solutions of the acetylspermidine.2HCl salts by their passage through AG3X4 resin (free base, 100–200 mesh) followed by thorough drying over phosphorous pentoxide ($P_2O_5$) under vacuum. Reductions were conducted for 18 hours in boiling tetrahydrofuran. After hydrolysis of excess hydride with aqueous HCl and removal of tetrahydrofuran by distillation, the reaction mixtures were made basic with sodium hydroxide (NaOH) and taken to dryness under vacuum. The products were extracted with ethanol and purified by ion exchange chromatography on CM sephadex C-25 (NH$^+_4$) using a linear gradient of 0 to 3.5 N NH$_4$OH. After removal of ammonium hydroxide (NH$_4$OH) by repeated evaporation under vacuum, the products were crystallized in about 50% yield by addition of methanol containing anhydrous HCl and recrystallized from water-methanol. Melting points of 282° C. and 284° C. were obtained for the $N^1$-and $N^8$-derivatives, respectively.

N,$^1$N$^8$-Boc-N$^4$-bromoacetylspermidine was prepared by treatment of the $N^1$,$N^8$-blocked spermidine with bromoacetyl bromide in dichloromethane in the usual manner (see Nagarajan et al. (1985) *J. Org. Chem.* 50:5735–5737) using triethylamine as a base. The resulting reaction solution was washed with dilute HCl, water and dilute NaHCO$_3$ and dried over Na$_2$SO$_4$. The residue after removal of solvent was dissolved in cold trifluoroacetic acid and deblocking was allowed to proceed for 20 minutes at room temperature. The excess acid was removed by evaporation under vacuum and a solution of the product in water was washed 3 times with chloroform. The product, $N^4$-bromoacetylspermidine.$2F_3CCOOH.H_2O$ was obtained as an oil upon drying (52% yield).

$N^1$,$N^8$-Boc—$N^4$-Acetylspermidine was obtained by heating $N^1$,$N^8$-Boc-spermidine with 4 equivalents of ethyl acetate at 100° C. in a sealed tube for 18 hours. After purification by flash chromatography (SiO$_2$, chloroform:methanol 9:1), the oily intermediate was deblocked with trifluoroacetic acid as outlined above. The product was purified by ion exchange chromatography on CM Sephadex C-25(NH$_4^+$) using a linear gradient of 0 to 3 molar (M) NH$_4$OH. After removal of NH$_4$OH by repeated evaporation under vacuum, $N^4$-acetylspermidine.$2HCl.0.5H_2O$, m.p. 171° C., was obtained in crystalline form from methanol containing anhydrous HCl and recrystallized from ethanol-pentane.

1-(3-Aminopropyl)-4-(aminomethyl)piperidine

A mixture of equimolar amounts of 4-(aminomethyl)-piperidine (Aldrich) and p-toluenesulfonic acid in ether was concentrated to a viscous oil under vacuum. This crude tosylate salt was dissolved in dichloromethane, 1 equivalent of 18-crown-6 (Aldrich) was added and the mixture was stirred at room temperature for 15 minutes. After removal of solvent, the residue was dried overnight under vacuum, redissolved in cold dichloromethane and treated with 1.1 equivalent of acrylonitrile (Kodak) under nitrogen. The mixture was allowed to warm to room temperature with stirring and stirring was continued overnight. Flash chromatography (silica (SiO$_2$), chloroform: methanol: NH$_4$OH 8:2:0.5) gave a yellow oil which was taken up in 10% NaOH and extracted with 4 portions of dichloromethane. The combined extracts were dried over sodium sulfate (Na$_2$SO$_4$), the solvent was removed and the intermediate 1-(3-cyanoethyl)-4-(aminomethyl)-piperidine was purified by flash chromatography (SiO$_2$, chloroform: methanol: NH$_4$OH 6:4:0.5). Hydrogenation of this intermediate was carried out in a 3.3:1 mixture of glacial acetic acid and acetic anhydride at 40 lbs/in$^2$ for 36 hours in the presence of platinum oxide catalyst. The catalyst was removed by filtration and the solvents evaporated under vacuum to yield an oil. The acetyl groups were removed from this diacetyl derivative by hydrolysis in 1.5N HCl for 24 hours at reflux temperature. The residue remaining upon removal of HCl crystallized under ether and was recrystallized from ethanol-ether to give the product 1-(3-aminopropyl)-4-(aminomethyl)-piperidine.3HCl-2H$_2$O, m.p. ~300° C., in 63% overall yield.

N-(3-Aminopropyl)-1,4-diaminocyclohexane

The trans and cis compounds were prepared in the same way starting with trans-1,4-diaminocyclohexane (Aldrich) and cis-1,4-diaminocyclohexane (~80% cis, mixture of cis and trans, Aldrich), respectively. To an ice-cold stirred solution of the diaminocyclohexane in ethanol under nitrogen was added 1 equivalent of acrylonitrile. The reaction mixture was allowed to warm to room temperature and stirring was continued at this temperature overnight. After removal of solvent, the intermediate N-cyanoethyl-1,4-diaminocyclohexane was isolated as an oil by flash chromatography (SiO$_2$, chloroform: methanol: NH$_4$OH 8:2:0.5). Hydrogenation of the intermediate was carried out in a 6.6:1 mixture of glacial acetic acid and acetic anhydride at 40 lbs/in$^2$ for 18 hours in the presence of platinum oxide catalyst. After removal of catalyst and solvents, 10% aqueous NaOH was added to the oily residue and the diacetyl derivative was extracted into chloroform. Removal of acetyl groups by refluxing the intermediate in 1.5N HCl for 12 hours yielded an oil upon removal of acid. The oil which crystallized under ether and was recrystallized form methanolether, provided the N-(3-aminopropyl)-1,4-diaminocyclohexane 3 HCl in approximately 20% overall yield, trans m.p. 315° C., cis (~80% of mixture) m.p. 293° C.

Fluorinated Spermidine Derivatives

The fluorinated derivatives of spermidine were synthesized and first tested as inhibitors of deoxyhypusine synthase by Annie Bernhardt and Dr. Pierre Mamont of the Marion Merrell Dow Research Institute in Strasbourg, France. Assays were with deoxyhypusine synthase from HTC cells under conditions similar to ours, except that the eIF-5A precursor protein was isolated from DFMO-treated HTC cells and the spermidine level was 1 μM. They found inhibitions of 90%, 86%, 35% and 0% with 6,6-difluorospermidine, 6-monofluorospermidine, 7-monofluorospermidine, and 7,7-difluorospermidine, respectively, at concentrations of 20 μM. The $K_i$ value obtained for 6,6-difluorospermidine was very close to that for 1,3-diaminopropane and to the $K_m$ value for spermidine. There are quantitative differences between these results and the findings given here. However, our observation that the spermidine derivative with fluoride on carbon 7 (compound 38) is devoid of inhibitory activity, whereas those with fluoride on carbon 6 (compounds 36 and 37) are quite strong inhibitors, is in agreement with the earlier findings.

Methods

The enzyme assay was performed as previously described (see Wolff et al. (1990) *J. Biol. Chem.* 265:4793–4799; and Park et al. (1991) *J. Biol. Chem.* 266:7988–7994). A typical assay mixture included 0.2M glycine, 1 mM dithiothreitol, 0.5 mM NAD+, 2.4 micromolar (μM) [1,8-³H] spermidine, 1 μM ec-eIF-5A(Lys), 25 micrograms (μg) bovine serum albumin, and 3–15 units of enzyme in a total volume of 20 microliters (μl). Incubations were carried out at pH 9.3 and 37° C. for 1 hour. The inhibitors were tested at 0.1 and 1 mM initially, then at lower concentrations as necessary to achieve less than 50% inhibition. Percent inhibition was plotted versus log inhibitor concentration in order to obtain graphic estimates of IC$_{50}$ values, i.e., the concentrations inhibiting [³H]deoxyhypusine production by 50%. The IC$_{50}$ values reported in the tables were calculated by fitting the data points to equation 1 where x=% inhibition and I is the inhibitor concentration.

$$IC_{50} = I \cdot \left( \frac{100 - x}{x} \right) \quad \text{eq (1)}$$

The nature of the inhibition was determined by plotting reciprocal velocities of [³H]deoxyhypusine production against reciprocals of [³H]spermidine concentrations at a constant fixed level of ec-eIF-5A(Lys) (1 μM) and at set inhibitor concentrations. With those inhibitors examined, linear plots were obtained and the patterns were indicative of competitive inhibition. Estimates of $K_i$ values were made by fitting the data to equation 2; wherein v is the velocity of the reaction, V is the maximum velocity, S is the substrate concentration, $K_m$ is Michaeli's constant, $K_i$ is the inhibition constant, and I is the inhibitor concentration.

$$v = \frac{V \cdot S}{K_m \left( 1 + \frac{I}{K_i} \right) + S} \quad \text{eq (2)}$$

All fits were performed by means of an interactive curve-fitting program, MLAB, developed and modified at the National Institutes of Health to run on an IBM personal computer.

In Vitro Testing

Figure 7:
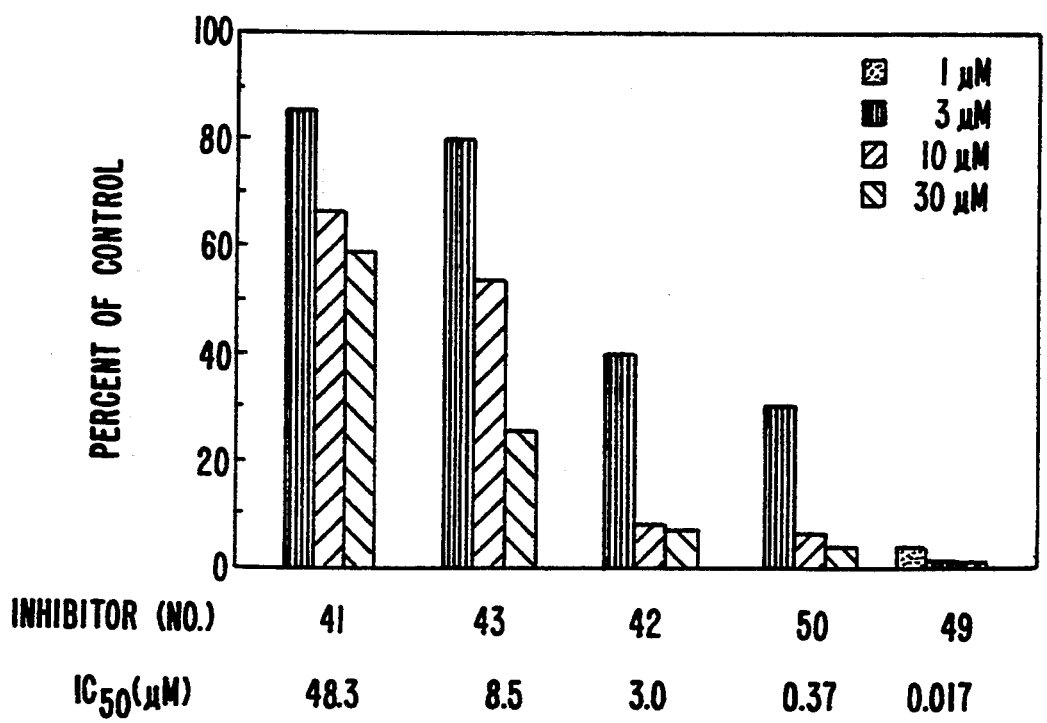
FIG. 7 is a graphical illustration of the effects of guanyldiamines on hypusine formation in Chinese hamster ovary cells. The cells were cultured in alpha modification of Eagle's medium supplemented with 10% horse serum. When the density of the cells reached $\sim 1 \times 10^6$ per 60 mm dish, 5 µCi per ml of [$^3$H]spermidine and the indicated concentrations (1, 3, 10, or 30 µM) of inhibitors were added. After continued incubation for 20 hours, the cells were washed and harvested. The protein-bound radiolabeled hypusine was determined as described previously (see Park et al. (1982) *J. Biol. Chem.* 257:7217–7222 and Park et al. (1981) *Proc. Natl. Acad. Sci. USA* 78:2869–2873). The amounts of hypusine formed are given as the percents of that in control cells without inhibitor. The inhibitors are designated by the numbers given in FIG. 5: 41, $N^1,N^6$-bisguanyl-1,6-diaminohexane; 43, $N^1,N^8$-bisguanyl-1,8-diaminooctane; 42, $N^1,N^7$-bisguanyl-1,7-diaminoheptane; 50, $N^1$-guanyl-1,8-diaminooctane and 49, $N^1$-guanyl-1,7-diaminoheptane. The IC$_{50}$ values are also from FIG. 5.

Several of the guanidino compounds were tested as inhibitors of hypusine formation in cultured Chinese hamster ovary cells. See Pegg (1988) *Cancer Res.* 48:759–774 and McCann et al. "Inhibition of Polyamine Metabolism Biological Significance and Basis for New Therapies" (1987) by Academic Press Inc. The results given in FIG. 7 show that each of these compounds inhibited radiolabeled hypusine formation from [³H]spermidine in these cells in culture. Significantly, the degree of in vivo inhibition by these compounds was found to be in direct correlation with their inhibition constants determined in vitro. These studies also revealed a direct correlation between prevention of hypusine formation in these cells by several guanyldiamines and their in vitro inhibition of deoxyhypusine synthase. This evidence for disruption of the initial step in the post-translational maturation of eukaryotic initiation factor 5A provides a basis for the potential control of protein biosynthesis and cell proliferation. Indeed, experiments underway show a similar relationship between in vitro inhibition and reduction in protein synthesis and in cell growth with no notable changes in cellular polyamine levels and no apparent signs of early toxicity (unpublished results).

Results

The data given in FIGS. 2–5 show the inhibitory effects of a number of compounds on the synthesis of radiolabeled deoxyhypusine from [³H]spermidine as catalyzed by deoxyhypusine synthase from rat testis. In FIG. 2 are given the IC$_{50}$ values, i.e., the concentrations of the compounds that provided 50% inhibition, for a series of diamines and polyamines of various carbon chain lengths. The apparent inhibition of labeling of [³H]deoxyhypusine by unlabeled spermidine (compound 10) is also included as a reference for comparison with diamines and other polyamines. Each of the compounds, for which kinetics of inhibition were examined, displayed inhibition of the competitive type. The $K_i$ values estimated for these compounds are also given in FIG. 2.

Of the three substrates for deoxyhypusine synthase, spermidine, NAD+ and eIF-5A precursor protein, the precursor protein is the most specific in the sense that this protein (and specifically a single lysine residue in this protein) is ustilized solely for hypusine production. This is evidenced by the finding that, when CHO cell are depleted of spermidine, eIF-5A precursor protein accumulates. (See Park (1987) *J. Biol. Chem.* 262:12730–12734 and Park (1988) *J. Biol. Chem.* 263:7447–7449.) However, a structurally related compound (a 16-membered peptide, modeled on residues 40–55 of the human eIF-5A precursor protein and encompassing the lysine residue, Lys[50], that is modified by deoxyhypusine synthase), was found to exert only weak inhibition and failed to act as a substrate. That this moderate sized peptide reacts only weakly, if at all, with the enzyme was seen as evidence that macromolecular features, rather than simple structural similarity, may be necessary for precursor protein-enzyme interaction.

Aliphatic Straight-Chain α,ω-Diamines and Polyamines

The efficiency of di- and polyamines as inhibitors of the enzyme varied depending on the number of methylene groups between their primary amino groups. With the exception of 1,3-diaminopropane (compound 2), which exerts product inhibition, and to a lesser extent putrescine (compound 3), the inhibition was maximal with compounds that resemble spermidine in carbon chain length. The presence of a secondary amino group in the molecule did not seem to be important as evidenced by the strong inhibition with 1,7-diaminoheptane (compound 6) and 1,8-diaminooctane (compound 7). In an extended conformation in which their amino groups are as far apart as possible, these two compounds resemble the fully extended form of spermidine in distance between primary amino groups, compound 6 being slightly shorter and compound 7 a bit longer. A similar relationship exists with caldine (compound 9) and N-(3-aminopropyl)cadaverine (compound 11), respectively, both of which provide some degree of inhibition. Interestingly, N-(3-aminopropyl)cadaverine was found to function as a substrate for deoxyhypusine synthase, albeit a poor one (see Park et al. (1991) *J. Biol Chem.* 266:7988–7994). Under the same conditions, caldine, however, displayed no detectable substrate property. The failure of spermine (compound 12) to function as an inhibitor may be a consequence of the relatively great distance between its primary amino groups.

Aliphatic Amines and Polyamines with a Single Primary Amino Group or with a Derivatized Primary Amino Groups(s)

Deoxyhypusine synthase does not appear to interact to any significant extent with monoamines (see Park et al. (1988) *J. Biol. Chem.* 263:15264–15269 and compound 13, FIG. 3). Therefore, if we make the plausible assumption that the enzyme has a binding site for each of the two primary amino groups of spermidine, it would appear that the distance between these two sites on the enzyme must be equal to or less than the maximum possible interamine group distance for 1,6-diaminohexane (compound 5) (8.7 Å) but greater than that for cadaverine (compound 4) (about 7.5 Å). This conclusion follows from the fact that diaminohexane displays inhibition, whereas cadaverine does not. α,ω-Diamines of greater chain length than diaminohexane (compounds 6–8) bind by assuming conformations in which their amino groups are closer together than they would be in their fully extended conformations. With these diamines hydrophobic interactions of their carbon chains with groups on the enzyme could contribute to binding and account for tighter association as a function of increasing carbon chain length within the spatial limits of the active site.

Parenthetically, it is not surprising that 1,3-diaminopropane (compound 2) and putrescine (compound 3) inhibit the enzyme, since the former is a product of the reaction (see Park et al. (1988) *J. Biol. Chem.* 263:15264–15269) and the latter, being of similar structure, may inhibit by interaction at the product site. It may be significant, however, that the inhibition by diaminopropane is competitive. When spermidine binds to the enzyme through its primary amino groups, it assumes a less than fully extended conformation in which its secondary amino group, which is not essential for binding, is directed, through precise alignment of its backbone structure, to the optimum position for catalysis. Those compounds of FIG. 3 that are closely related in structure to spermidine, with the exception of having a single primary amino group (compounds 14–17) or one or both primary amino groups derivatized (compounds 18–21), show no inhibition.

The failure of these spermidine analogs to react with enzyme is consistent with the suggested mode of spermidine-enzyme interaction. N-(3-Aminopropyl)cadaverine (compound 11), which contains one more methylene group than spermidine, occupies the spermidine site on the enzyme by virtue of a conformation not unlike that of spermidine, i.e., with its primary amino groups arranged at the same distance apart as those of spermidine, but in which its secondary amino group is necessarily less precisely fit to the site of catalytic cleavage. Therefore, this polyamine functions as a substrate, albeit a poor one. Caldine (compound 9), on the other hand, is one methylene group shorter than spermidine and, although it binds in the manner described above, its secondary amino group cannot extend far enough toward the point for catalysis on the enzyme to allow contact. Hence, caldine fails to serve as a substrate. Derivatization of the primary amino groups of caldine, as in compounds 22–24, or those of 1,8-diaminooctane (see compound 25) causes a loss in binding, an effect similar to that seen with spermidine.

The compounds listed in FIG. 3, each of which is closely related to spermidine, but in each of which either one or both primary amino groups are omitted, substituted or derivatized, showed no significant degree of inhibition. Together the findings of FIGS. 2 and 3 suggest that a compound must possess two properly oriented unsubstituted primary amino groups in order to function as an effective inhibitor.

Polyamines with Substitutions on the Secondary Amino Group or in the Carbon Chain The inhibitory properties of polyamines with alterations in their backbone structures are given in FIG. 4. The introduction of a variety of substituents in place of hydrogen on the secondary amino group of spermidine (compounds 26–29) and placement of a methyl group on this amino group of caldine (compound 30) produced compounds devoid of inhibitory activity. Certain other changes in the backbone structure of spermidine were found to have similar effects. Limiting the flexibility, together with increasing the size, of the butylamine portion of spermidine by introduction of cyclic structures (compounds 31–33) or simply increasing the size of this portion of spermidine by adding two methyl groups on a single carbon atom (compound 34) abolished inhibition. Some degree of inhibition was exerted by a spermidine derivative with one methyl group on the carbon adjacent to the terminal propylamine group (compound 35). 1-Methyl spermidine (compound 35) may exert the degree of inhibition observed by simply binding in the direction opposite to that in which spermidine binds, i.e., with its methyl group outside the binding pocket. Interference in binding by the methyl group would be averted by its projection away from the enzyme surface.

1-(3-Aminopropyl)-4-aminomethylpiperidine (compound 31) and N-(3-aminopropyl)-1,4-diaminocyclohexane (the cis and trans forms, compounds 32 and 33, respectively) of FIG. 4, each of which is closely related in structure to spermidine, all possess a saturated six-membered ring that exerts a degree of restriction in movement to the four-carbon segment corresponding to the butyl portion of spermidine. In addition, these ring structures add significant mass that could provide steric hinderance sufficient to interfere with attachment to enzyme, as could be the case with the gem methyl groups of 5,5-dimethylspermidine (compound 34). That none of these compounds is able to attach to the active site of deoxyhypusine synthase is evident from their failure to inhibit the enzyme. Each can assume conformations in which the centers of its two primary amino groups are oriented at distances apart of from 7.5 to 8.7 Å, distances compatible with attachment at the enzyme's active site. Thus, the cause for their failure to bind to enzyme is not immediately evident. The finding that several $N^4$-substituted spermidines (compounds 26–29) and $N^4$-methylcaldine (compound 30) also do not interact with the active site of the enzyme adds a further dimension to this perplexity. Clearly, if there were no restricted region on the enzyme between the two primary amine sites required for spermidine binding, each of these compounds could bind by virtue of direction of its bulky group or groups away from the enzyme surface. Even if a substrate-induced specific conformational change in enzyme essential for catalysis were disallowed as a consequence of structural restrictions within these small molecules, or by the size of groupings on these molecules, this would not curtail binding since this rearrangement in the enzyme's active site would occur subsequent to binding.

Fluorinated analogs of spermidine in which the fluoride was on carbon 6 (compounds 36 and 37) provided effective inhibition, whereas an analog with fluoride on carbon 7 (compound 38) displayed no inhibition. A derivative of spermidine in which oxygen replaced the methylene group adjacent to the terminal butylamine group (compound 39) was without effect.

Because of the small size of fluorine, almost isosteric to hydrogen, and the short C-F bond (Walsh, C. (1983) *Adv. Enzymol.* 55:197–285), substitution of this atom for hydrogen atoms in the methylene chain of spermidine gives polyamines very closely related in size and structure to spermidine. However, the amino functions of these fluoride-containing polyamines are quite different from those of spermidine as a consequence of the strong electron-withdrawing property of the fluoride atom (see Baillon et al. (1988) *Eur. J. Biochem.* 176:237–242). The notion that protonation of the amino groups at both positions 1 and 8 of spermidine is essential for its binding to the active site of the enzyme is suggested by the findings with the fluorinated spermidines. 7,7-Difluorospermidine (compound 38), the $N^8$-amino group of which has a $pK_a$ value of 6.64 (id.) and thus is almost entirely deprotonated under the conditions of pH used for inhibition studies, i.e., pH 9.3, displays no inhibition. On the other hand, 6-fluorospermidine (compound 36) and 6,6-difluorospermidine (compound 37), both of which act as inhibitors and are therefore close enough in structure to spermidine to bind to enzyme, are protonated to a large degree at their primary amino groups at pH 9.3. The reported $pK_a$ values of the $N^1$- and $N^8$-amino groups, respectively, are 10.40 and 9.55 for 6-fluorospermidine and 10.34 and 9.29 for 6,6-difluorospermidine, as compared to 9.94 and 10.81 for spermidine (id.). Consistent with the idea that both primary amino groups of spermidine must be in the charged form for binding to enzyme is the fact that all of the longer-chain diamines that function as inhibitors (compounds 5–8) are largely protonated at both amino groups at pH 9.3; the $pK_a$ values of their amino groups vary between 10 and 13. In addition, N-(3-aminooxypropyl)-1,3-diaminopropane (compound 39), an isosteric analog of spermidine whose aminooxy group of $pK_a$ 4.5–5.0 is essentially deprotonated at pH 9.3 (see Khomutov et al. (1963) in "Chemical and Biological Aspects of Pyridoxal Catalysis" (Snell, E. E., Fasella, P. M., Braunstein, A., and Rossi-Fanelli, A., eds.), Pergamon Press, London, pp. 313–322) does not function as an inhibitor. It seems worth mention that the failure of this specific aminooxy compound to inhibit the enzyme indicates that deoxyhypusine synthase-catalyzed cleavage of spermidine does not proceed through a pyridoxal-linked reaction. Aminooxy substrate analogs have proven to be excellent reversible inhibitors of pyridoxal phosphate cofactor enzymes because they form very stable Schiff base adducts with the cofactor (see Khomutov et al. (1963) in "Chemical and Biological Aspects of Pyridoxal Catalysis" (Snell, E. E., Fasella, P. M., Braunstein, A., and Rossi-Fanelli, A., eds.), Pergamon Press, London, pp. 313–322).

Guanylated Diamines and Polyamines

The fungicide guazatine, a guanylated polyamine derivative known to inhibit pea seedling diamine oxidase and oat seedling polyamine oxidase (see Smith (1983) *Methods Enzymol.* 94:311–314.), has been reported to be a strong inhibitor of deoxyhypusine synthase (see Murphey et al. (1987) *J. Biol. Chem.* 262:15033–15036). This finding is somewhat surprising in that a close structural relationship of guazatine (compound 40, FIG. 5) to spermidine is not apparent.

The $IC_{50}$ and $K_i$ values for a number of guanylated diamines and polyamines as inhibitors of deoxyhypusine synthase are given in FIG. 5. Interestingly, whereas the bisguanylated derivatives of 1,6-diaminohexane, 1,7-diaminoheptane, and 1,8-diaminooctane (compounds 41, 42, and 43, respectively) acted as inhibitors of deoxyhypusine synthase, the bisguanylated form of the strongly inhibitory diamine product of enzymatic spermidine cleavage, 1,3-diaminopropane (compound 44) provided no inhibition. $N^1,N^8$-bisGuanyl-1,8-diaminooctane (compound 43), the carbon chain of which corresponds in length to that between the secondary amino group of guazatine and either of its guanidino groups, is somewhat stronger an inhibitor than guazatine (compound 40), showed no better inhibition than the parent diamine, 1,8-diaminooctane (compound 7). An enhancement in inhibitory potency by bisguanylation occurred with 1,6-diaminohexane (compound 5) and 1,7-diaminoheptane (compound 6), however, where the $IC_{50}$ was lowered 2-to 3-fold (compare compounds 41 and 5, and 42 and 6). In contrast, bisguanylation of the polyamine caldine (compound 9) resulted in a somewhat reduced inhibition as shown by the increase of 5-fold in $IC_{50}$ (compare compounds 45 and 9).

In an effort to obtain an explanation for these differential effects of bisguanylation on inhibition and in order to determine the extent of guanylation needed to influence inhibition, we chose to test the monoguanylated forms of several of the compounds. The monoguanylated derivative of 1,3-diaminopropane (compound 46), like its bisguanylated form (compound 44) was without inhibitory property, whereas agmatine (compound 47) displayed a moderate degree of inhibition. On the other hand, $N^1$-guanylcaldine (compound 48), $N^1$-guanyl-1,7-diaminoheptane (compound 49) and $N^1$-guanyl-1,8-diaminooctane (compound 50) proved to be excellent inhibitors, far exceeding the parent amines, as well as their bisguanylated counterparts, in inhibitory potency. In line with this result was the finding that both of the monoguanylated spermidine (compounds 51 and 52) exceeded bisguanylated spermidine (compound 53) as inhibitors, although the differences in inhibitory properties were not as pronounced as were those between the other mono- and bisguanylated compounds. $N^1$-guanyl-1,7-diaminoheptane (compound 49) provided the strongest inhibition of the compounds tested. The $K_i$ value for this compound was estimated as $9.7\pm0.50$ nM, about 450-fold less than the apparent $K_m$ for spermidine ($4.5\pm0.7$ μM).

To our knowledge there are no other reported instances of monoguanylated compounds providing greater effects than their bisguanylated counterparts. Indeed, the very specific nature of the present finding and its significance are underscored by a number of published studies in which the bisguanylated compounds consistently exerted the greater influence (see, e.g., Oriol-Audit (1978) *Eur. J. Biochem.* 87:371-376; Shindo et al. (1979) *Neuroscience (Kobe, Japan)* 5:96-97; Darrko et al. (1986) *Biophys. J.* 49:509-519; and David et al. (1992) *J. Biol. Chem.* 267:1141-1149).

Because of their similarities in structure to spermidine and their high affinities for the enzyme, the monoguanylated spermidines (compounds 51 and 52) were tested as substrates for deoxyhypusine synthase. Neither displayed any detectable substrate property under conditions similar to those employed to demonstrate that N-(3-aminopropyl)cadaverine acts as a substrate (see Park et al. (1991) *J. Biol. Chem.* 266:7988-7994).

Figure 6:
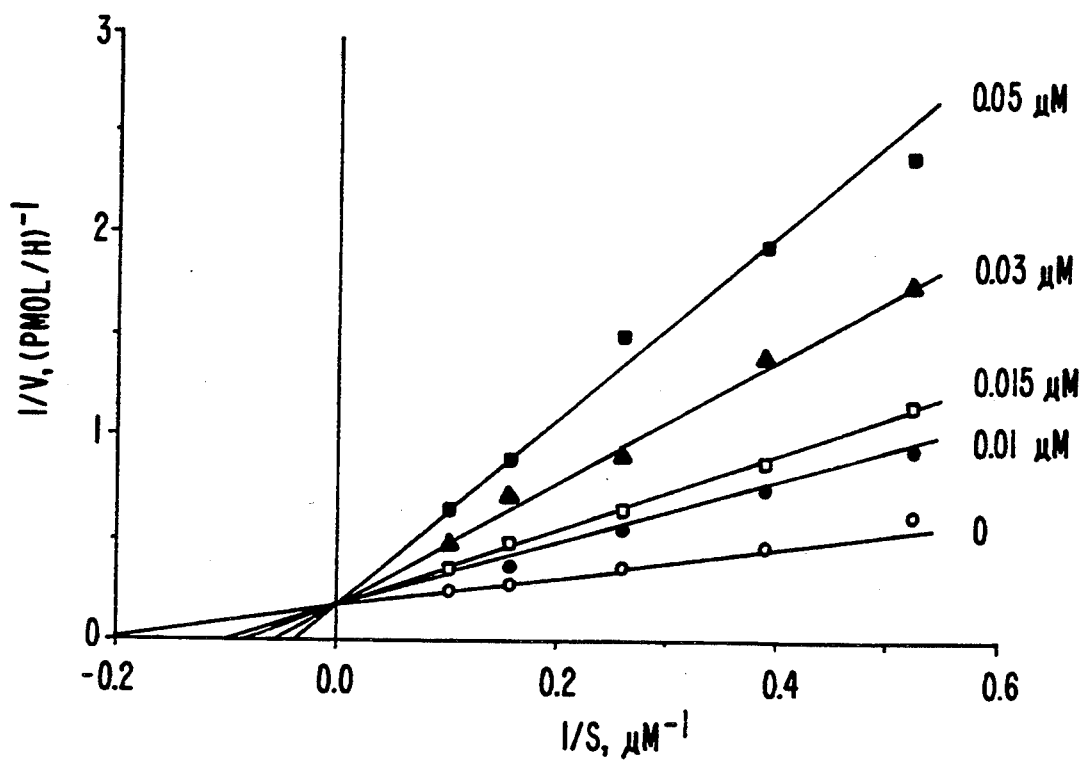
FIG. 6 is a graphical illustration of the inhibition pattern for rat testis deoxyhypusine synthase with [$^3$H]spermidine as varied substrate and $N^1$-guanyl-1,7-diaminoheptane as inhibitor. The level of eIF-5A precursor protein, ec-eIF-5A(Lys), was fixed at 1 µM. The inhibitor concentrations (0.05, 0.03, 0.015, 0.01 or 0.0 µM) are given in µM at the ends of the lines. The initial velocities are given in [$^3$H]deoxyhypusine formed (per 6 units of enzyme).

FIG. 6 illustrates a representative example of the relationship between the concentrations of the substrate [$^3$H]spermidine and employing one of the inhibitors, $N^1$-guanyl-1,7-diaminoheptane (compound 49). This pattern is representative of those obtained with other inhibitory compounds of FIGS. 2 and 5. Since each of the inhibitors in FIG. 5 acts in a competitive manner against spermidine and because in general each of those bisguanylated compounds (compounds 41, 42, 43, and 45) that is an inhibitor displays inhibition not widely different from its parent amine (compounds 5, 6, 7, and 9, respectively), it seems logical to conclude that the guanidino group can be accommodated at each of the two sites on the enzyme that bind the primary amino groups of spermidine. It seems likely, however, from the uniformly more efficient inhibition exerted by the monoguanylated diamines (compounds 49 and 50) and polyamines (compounds 48, 51, and 52) that one of the sites favors a guanidino group over an amino group, while the other prefers the amino group. That this preference for an amino group is very strong is inferred by the finding that certain monoguanylated compounds are many-fold more effective inhibitors than their bisguanylated counterparts, e.g., $N^1$-guanyl-1,7-diaminoheptane ($K_i=0.0097$ μM) versus $N^1,N^7$-bisguanyl-1,7-diaminoheptane ($K_i=1.2$ μM). It is tempting to suggest that it is this site, i.e., the one which prefers the amino group, to which the terminal propylamine group of spermidine is directed in its productive binding to enzyme. This suggestion derives from the fact that no inhibition was detected with either $N^1$-guanyl-1,3-diaminopropane (compound 46) or with $N^1,N^3$-bisguanyl-1,3-diaminopropane (compound 44), both of which are derivatives of 1,3-diaminopropane, the strongly inhibitory product of the enzymatic cleavage.

The mild degree of inhibition exerted by agmatine (compound 47) is not inconsistent with this supposition since its interaction could occur at the position on the enzyme in which the butylamine moiety of spermidine is normally arranged, i.e., with its guanidino group directed toward the site that favors this group over the amino group. It follows from this suggestion, incidentally, that putrescine and 1,3-diaminopropane inhibit by binding at different positions on the enzyme, each occupying a separate portion of the spermidine-binding site. That $N^8$-guanylspermidine (compound 52) is a somewhat more effective inhibitor than $N^1$-guanylspermidine (compound 51) is in accordance with an idea that because of the preferences and arrangement of the two binding sites for the primary amino groups of spermidine, this polyamine and its $N^8$-guanyl derivative attach to enzyme in a similar fashion. However, despite its high affinity for the enzyme, the spermidine derivative apparently is not aligned on the enzyme in exactly the same way as is spermidine. If it were, it would function as a substrate which it does not. Perhaps the difference in alignment on the enzyme is due to the greater size of the guanidinium group and/or its tendency to form multiple zwitterionic hydrogen bonds with anionic ligands (see, e.g. Dietrich et al. (1979) *Helv. Chim. Acta* 62:2763-2787; and Makhatadze et al. (1992) *J. Mol. Biol.* 226:491-505), which may restrict the conformation of either the guanidinium compound or the protein.

The disclosures in this application of all articles and references, including patent documents, are incorporated herein by reference.

It is to be understood that the above description is intended to be illustrative and not restrictive. Many embodiments will be apparent to those of skill in the art upon reviewing the above description. The scope of the invention should, therefore, be determined not with reference to the above description, but should instead be determined with reference to the appended claims, along with the full scope of equivalents to which such claims are entitled.

What is claimed is:

1. A method for inhibiting the growth of mammalian cells, said method comprising administering a deoxyhypusine synthase inhibitor to the mammalian cells, wherein the deoxyhypusine synthase inhibitor is a compound having the general formula:

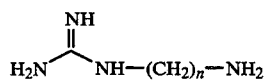

wherein n is an integer from four to nine.

2. A composition for inhibiting the growth of mammalian cells, which composition comprises a deoxyhypusine synthase inhibitor in a pharmaceutically acceptable carrier, wherein the deoxyhypusine synthase inhibitor is a compound having the general formula:

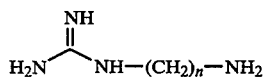

wherein n is an integer from four to nine.

3. A method for screening mammalian cells to determine their susceptibility to treatment with a deoxyhypusine synthase inhibitor comprising the steps of:
   a) isolating the cells from a patient;
   b) treating the cells with a deoxyhypusine synthase inhibitor composition of claim 2; and
   c) determining the inhibitor's effect on the cells.

4. A diagnostic kit comprising a deoxyhypusine synthesis inhibitor composition of claim 2 and other reagents, including a means for detecting the effectiveness of the inhibitor composition.

5. A compound having the formula:

$$H_2N-(CH_2)_n-NH-(C=NH)-NH_2$$

where n is seven or eight.

* * * * *